United States Patent [19]

Sogard et al.

[11] Patent Number: 5,447,497
[45] Date of Patent: Sep. 5, 1995

[54] BALLOON CATHETER HAVING NONLINEAR COMPLIANCE CURVE AND METHOD OF USING

[75] Inventors: David J. Sogard, Edina; Gary L. Hendrickson, New Hope; Lixiao Wang, St. Paul; Pete T. Keith, Fridley, all of Minn.

[73] Assignee: Scimed Life Systems, Inc, Maple Grove, Minn.

[21] Appl. No.: 243,473

[22] Filed: May 16, 1994

Related U.S. Application Data

[63] Continuation of Ser. No. 927,062, Aug. 6, 1992, abandoned.

[51] Int. Cl.$^6$ ............................................. A61M 29/02
[52] U.S. Cl. ................................ 604/101; 604/53; 606/194
[58] Field of Search ..................... 604/96, 101, 53; 606/191, 192, 194

[56] References Cited

U.S. PATENT DOCUMENTS

| | | | |
|---|---|---|---|
| 2,690,595 | 10/1954 | Raiche . | |
| 4,271,839 | 1/1981 | Fogarty et al. . | |
| 4,327,736 | 5/1982 | Inoue | 128/349 B |
| 4,338,942 | 7/1982 | Fogarty | 128/344 |
| 4,403,612 | 9/1983 | Fogarty | 128/344 |
| 4,608,984 | 9/1986 | Fogarty . | |
| 4,637,396 | 1/1987 | Cook | 128/344 |
| 4,649,914 | 3/1987 | Kowalewski | 128/207.15 |
| 4,744,366 | 5/1988 | Jang | 128/344 |
| 4,820,349 | 4/1989 | Saab . | |
| 4,932,958 | 6/1990 | Reddy et al. | 606/192 |
| 4,983,167 | 1/1991 | Sahota | 606/194 |
| 5,049,131 | 9/1991 | Deuss | 604/96 |
| 5,057,092 | 10/1991 | Webster, Jr. | 604/282 |
| 5,090,958 | 2/1992 | Sahota | 604/98 |
| 5,108,370 | 4/1992 | Walinsky | 604/96 |
| 5,290,306 | 3/1994 | Trotta et al. . | |
| 5,304,135 | 4/1994 | Shonk . | |
| 5,342,305 | 8/1994 | Shonk . | |
| 5,358,487 | 10/1994 | Miller . | |

FOREIGN PATENT DOCUMENTS

| | | |
|---|---|---|
| 0274411A2 | 7/1988 | European Pat. Off. . |
| 420488 | 4/1991 | European Pat. Off. . |
| 0540858A1 | 5/1993 | European Pat. Off. . |
| 0420488B1 | 7/1993 | European Pat. Off. . |
| 0582870 | 2/1994 | European Pat. Off. . |
| 92/19440 | 11/1992 | WIPO . |

OTHER PUBLICATIONS

"PTCA Balloon Materials, Their Characteristics and Impact on Catheter Selection", *Technical Notes* by Daniel O. Adams BME.
Modern Plastics Encyclopedia 1986–1987, p. 82.
Encyclopedic Dictionary of Chemical Technology, Norther, et al. VCH (1993) p. 288.
Effect of Inflation Pressures on Coronary Angioplasty Balloons, Avanindra Jain, MD, Linda L. Domer, MD, Albert E. Raizner, MD, and Robert Roberts, MD., (*The American Journal of Cardiology* 1986; 57:26–28).
Improved Dilatation Catheter Balloons, Stanley B. Levy, Ph.D., *J. Clinical Engineering*, 11, 291–296 (1986).

*Primary Examiner*—Corinne Maglione
*Attorney, Agent, or Firm*—Vidas, Arrett, & Steinkraus

[57] ABSTRACT

A balloon catheter, having a non-linear compliance curve, made up of a dual layered balloon, one balloon being a Compliant balloon and the other balloon being a Non-Compliant balloon.

32 Claims, 4 Drawing Sheets

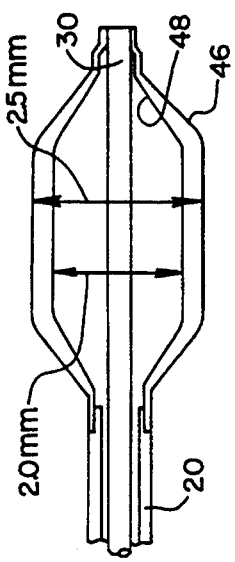
Fig. 7
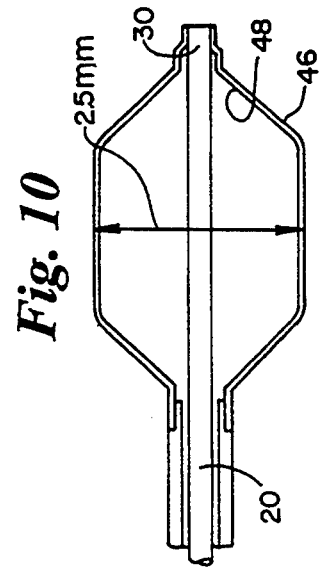
Fig. 10
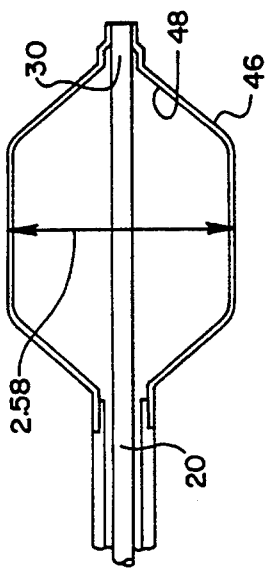
Fig. 13
Fig. 6
Fig. 9
Fig. 12
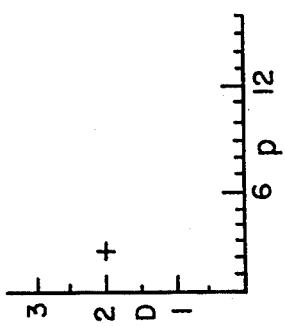
Fig. 5
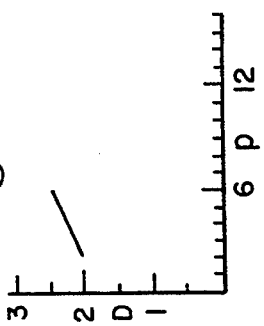
Fig. 8
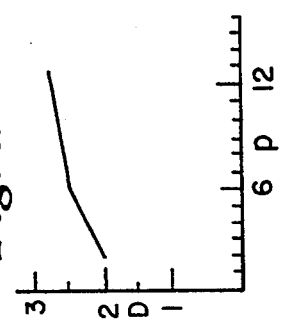
Fig. 11

BALLOON CATHETER HAVING NONLINEAR COMPLIANCE CURVE AND METHOD OF USING

This is a continuation of application Ser. No. 07/927,062 filed on Aug. 6, 1992, now abandoned.

BACKGROUND OF THE INVENTION

The present invention relates generally to balloon catheters used for angioplasty.

Angioplasty, an accepted and well known medical practice involves inserting a balloon catheter into the blood vessel of a patient, maneuvering and steering the catheter through the patient's vessels to the site of the lesion with the balloon in an un-inflated form. The un-inflated balloon portion of the catheter is located within the blood vessel such that it crosses the lesion or reduced area. Pressurized inflation fluid is metered to the inflatable balloon through a lumen formed in the catheter to thus dilate the restricted area. The inflation fluid is generally a liquid and is applied at relatively high pressures, usually in the area of six to twelve atmospheres. As the balloon is inflated it expands and forces open the previously closed area of the blood vessel. Balloons used in angioplasty procedures such as this are generally fabricated by molding and have predetermined design dimensions such as length, wall thickness and nominal diameter. Balloon catheters are also used in other systems of the body for example the prostate and the urethra. Balloon catheters come in a large range of sizes and must be suitably dimensioned for their intended use.

The term, low pressure diameter, as used herein with reference to the balloon catheter, means the diameter of the balloon when it is inflated to two (2) atmospheres.

The term, expanded diameter, as used herein with reference to the balloon catheter, means the diameter of balloon when it is inflated to six (6) to (12) atmospheres.

All angioplasty balloons have a minimum pressure at which they will burst called the minimum burst pressure. The physician is aware of the minimum burst pressure angioplasty balloons that he or she uses and usually avoids inflating a balloon to the point where it bursts. The physician is also aware that each kind and size of angioplasty balloon has its own expansion characteristics. This characteristic is usually expressed as a number which is the decimal portion of a millimeter that the balloon will expand when one additional atmosphere of pressure is applied. For example a 3 millimeter (diameter) balloon may expand 0.10 millimeters for each additional atmosphere of pressure that is applied. In this example at 10 additional atmospheres of pressure the balloon would have a diameter of 4.00 millimeters. This stretching characteristic is a factor of both the wall thickness and the material from which the balloon is molded. If the diameter of a balloon is measured during inflation, and the diameter is plotted, as one coordinate, against the inflation pressure as the other coordinate, the resulting curve is called the compliance curve for that particular balloon. If a balloon is made of a material that results in a relatively large increase in diameter when the balloon is inflated to its expanded diameter, such a balloon is said to be a High-Compliant balloon, or is said to be a balloon with a high compliance curve. FIG. 1A, is a graph showing a set of compliance curves for catheter balloons. In FIG. 1A the inflation pressure, measured in atmospheres, is plotted along the X-axis and the balloon diameter measured in millimeters is plotted along the Y-axis. In FIG. 1A the compliance curve having the greatest inclination is labeled High-Compliant. A High-Compliant balloon has a relatively large increase in diameter in response to an increase in inflation pressure. It should be noted that balloons defined herein as High-Compliant balloons are commonly referred to in the trade as, "Compliant balloons" or balloons made from compliant plastic material.

If a balloon is made of a material that results in a relatively small increase in diameter when the balloon is inflated to its expanded diameter, such a balloon is said to be a Non-Compliant balloon, a balloon made from non compliant plastic material or a balloon with a low compliance curve. Referring to FIG. 1A, the compliance curve having the least inclination is labeled Non-Compliant. A Non-Compliant balloon has a relatively small increase in diameter in response to an increase in inflation pressure. In FIG. 1A the third compliance curve is labeled Intermediate Compliant and represents a balloon having compliant characteristics between High and Non-Compliant balloons. It should be noted that although only three compliance curves are shown in FIG. 1A, balloons having compliant anywhere between the High-Compliant and the Non-Compliant curves are available. It should also be noted that all compliance curves shown in FIG. 1A are linear (straight lines).

High-Compliant balloons are made from relatively soft or flexible polymeric materials. Examples of these materials are thermoplastic polymers, thermoplastic elastomers, polyethylene (high density, low density, intermediate density, linear low density), various co-polymers and blends of polyethylene, ionomers, polyesters, polyurethanes, polycarbonates, polyamides, polyvinyl chloride, acrylonitrile-butadiene-styrene copolymers, polyether-polyester copolymers, and polyether-polyamide copolymers. A suitable copolymer material, polyolefin material is available from E. I. DuPont de Nemours and Co. (Wilmington, Del.), under the tradename Surlyn ® Ionomer.

Intermediate-Compliant balloons are made of polyethylene and nylon materials.

Non-Compliant balloons are made from relatively rigid or stiff polymeric materials. These materials are thermoplastic polymers and thermoset polymeric materials. Some examples of such materials are poly(ethylene terephthalate), polyimide, thermoplastic polyimide, polyamides, polyesters, polycarbonates, polyphenylene sulfides, polypropylene and rigid polyurethanes. Non-Complaint balloons made from poly(ethylene terephthalate) are commonly referred to as PET balloons.

The compliant characteristics of an angioplasty balloon affects how the physician uses the balloon catheter. A Non-Compliant balloon, will increase in diameter by a maximum of 5% of its nominal diameter in response to increasing the pressure to as much as twenty atmospheres. Sixteen atmospheres is safely below the burst pressure of such a Non-Compliant balloon. However, when inflated to its expanded diameter, a Non-Compliant balloon becomes very hard.

When a physician encounters a lesion that has become calcified and is very hard and rigid he may select a Non-Compliant balloon, that will become very hard and function to crack the rigid calcified lesion. Non-Compliant balloons have the advantage over Compliant balloons in that they can be used to dilate and crack hard lesions. Also if a Non-Compliant balloon is located in a vessel, across a restricted area of the vessel, and an end or both ends extend into non restricted areas of the vessel, the pressure in the balloon can be increased in the balloon sufficient to dilate or crack the restricted area without risking the possibility of damaging adjacent non restricted portions of the vessel. Non-Compliant balloons have the disadvantage that they are not effective if the normal vessel size lies between the size range of the available Non-Compliant balloons. Another disadvantage of Non-Compliant balloons is that if the lesion or restriction recoils after being dilated to its desired diameter, the Non-Compliant balloon cannot be used to dilate the lesion or restriction to a diameter greater than the previous dilation to thus overcome the recoil.

A High-Compliant balloon, will increase in diameter 15% to 40% in response to increasing the inflation pressure to a point safely below its burst pressure. The advantage of a High-Compliant balloon over a Non-Compliant balloon is that fewer models of High-Compliant balloons are required to fill a range of sizes. Non-Compliant balloons are typically available in size increments of 0.25 mm while High-Compliant balloons typically have size increments of 0.50 mm. Also an off-sized artery (i.e. 2.90 mm) will be difficult to dilate with a Non-Compliant balloon. Another advantage of a High-Compliant balloon over a Non-Compliant balloon is that if a restriction, after being dilated to its desired diameter, recoils when the balloon is deflated, the High-Compliant balloon can be re-inflated to a higher pressure thus dilating the restriction to a diameter greater than its desired diameter resulting in a satisfactory post recoil lumen diameter. This process can be repeated until the restriction retains its desired diameter after deflation of the balloon. High-Compliant balloons also have disadvantages, for example they can not be successfully used to dilate a hard lesion. Also if a High-Compliant balloon is located across a restriction and an end or both ends of the balloon extend into non restricted areas, when high pressure is applied to the balloon, the pressure may not be sufficient to crack or dilate the restrict area but will dilate the non restricted area to diameters greater than their normal diameter. In this situation damage can be done to the non restricted portions of the vessel.

The advantage of a hybrid compliant balloon is that advantages of both the Compliant and Non-Compliant balloons can be obtained in a single catheter that can be sized to the artery by varying the inflation pressure. In situations where the pressure required for a successful dilation is not extraordinarily high, a hybrid compliant balloon will give the physician more flexibility in matching the balloon to the artery size, resulting in a more controlled dilation.

In some situations a physician may desire a High-Compliant balloon that can initially expanded a significant amounts. If after the blood vessel adjacent to the restriction has been dilated to its natural size or at most 10% larger than its natural size, and the lesion has not yielded completely, it is not desirable that the balloon size be further increased due to the high rate of restenosis and dissection. In a situation such as this the physician may, after the restriction has not yielded sufficiently with the High-Compliant balloon, desire to remove the High-Compliant balloon and replace it with a Non-Compliant balloon. The Non-Compliant balloon that would be selected in this situation would have a nominal diameter approximately equal to the natural diameter of the open blood vessel, and its desired function would be to tightly compress the lesion into the wall of the blood vessel. It is desirable in this situation that the inflated balloon becomes very hard and rigid but not expand to a diameter that is greater than the natural diameter of the blood vessel. To accomplish this with currently available balloon catheters the initial High-Compliant balloon must be removed and replaced with a Non-Compliant balloon. This has the disadvantage that the patient is exposed to the trauma of removing and replacing a balloon catheter, the procedure time is lengthened and there is the expense of two balloon catheters. These disadvantages can be avoided by use of a balloon catheter having a hybrid compliant curve of the type disclosed in the preferred embodiment of this invention.

In another situation, with a hard calcified lesion, a physician may desire a Non-Compliant balloon which is inflated to whatever high pressure is required to yield or crack the lesion. If upon deflation of the Non-Compliant balloon the vessel retains its dilated diameter then the procedure has been successful and the catheter is removed. If however the vessel recoils, then the physician may desire to 'over expand' the lesion site to a diameter greater than the normal diameter of the vessel. A Compliant balloon would be selected in this situation, and since the lesion has been cracked, the lesion area can now be dilated to a diameter greater than its normal diameter through the application of pressures that will not damage the adjacent non restricted vessel. To accomplish this with currently available balloon catheters the initial Non-Compliant balloon must be removed and replaced with the second Compliant balloon. This has the disadvantage that the patient is exposed to the trauma of removing and replacing a balloon catheter, the procedure time is lengthened and there is the expense of two balloon catheters. These disadvantages can be avoided by use of a balloon catheter having a hybrid compliant curve of the type disclosed in an alternate embodiment of this invention.

Compliance curves of angioplasty balloons, in their usable range are linear, that is essentially a straight line. As a result a physicians choice, in the past, has been to select a balloon having a linear compliance curve that best meets his needs. Physicians often encounter medical situations where an angioplasty balloon having a nonlinear compliance curve is called for but balloon catheters with the desired compliance curve have not been available. For example a physician may have a medical situation in which he desires a balloon that will initially increase in diameter by 20% and then become very rigid and hard with little further increase in diameter. Another example would be the situation where two lesions are encountered, one that can be treated with a High-Compliant balloon and the other that requires a Non-Compliant balloon. Still, another example would be the situation where the physician encounters a medical situation in which he desires to initially dilate a hard lesion to the normal diameter of the vessel but does not know whether the dilated vessel will recoil. Balloon catheters having hybrid or nonlinear compliance curves that could satisfy the requirements of these examples are possible as a result of this invention.

FIG. 2A is a graph in which the balloon diameter, in millimeters, is plotted along the Y-axis and the pressure in atmospheres is plotted along the X-axis. FIG. 2A, shows the compliance curves for two particular balloon catheters. In FIG. 2A the compliance curve having the greatest inclination is labeled High-Compliant and the compliance curve having the lesser inclination is labeled Non-Compliant. In accordance with the subject invention a two layered balloon is used, one of the balloons being a High-Compliant balloon and the other being a Non-Compliant balloon. Inflation fluid is metered through the inflation lumen to the inner balloon. In the preferred embodiment the High-Compliant balloon is inflates during the initial inflation phase, for example from its low pressure diameter to a diameter equal to its low pressure diameter times 1.2. During this initial inflation phase the relatively steep slope of the compliance curve labeled High-Compliant is followed. When the pressure is increased above the point at which the High-Compliant balloon has expanded to a diameter equal to 1.2 times its low pressure diameter, then the second inflation phase begins and the Non-Compliant balloon begins to expand, however it follows the relatively shallow slope of the compliance curve labeled Non-Compliant. The result is, as shown by the compliance curves shown in full lines in FIG. 2A. The full line compliance curve of FIG. 2A is a non linear compliance curve which is a hybrid of the compliance curves of the two balloons.

The prior art includes several patents that disclose double layered catheter balloons however the purposes for the double layer balloons in these prior art patents are different than the purpose for the double layer balloon arrangement of this invention. The prior art discloses the concept of independently inflatable, concentric balloons having different diameters. The smaller balloon is inflated first and if additional dilation is required the larger balloon is inflated. The purpose for other prior art double balloons is to provide for a small profile when the balloon is un-inflated, one balloon functioning as a holding chamber for the other or to facilitate the unfurling and inflation of the balloon when it is located in a lesion. Such prior art patents are U.S. Pat. Nos. 4,744,366; 4,649,914; 4,637,396; 4,608,984; 4,403,612; 4,338,942 and 4,327,736.

It is a primary objective of the present invention to provide a balloon catheter having a nonlinear compliance curve that has a particular use in a medical procedure.

Another objective of the present invention is to provide a balloon catheter having a two layered balloon in the inflation area that has a nonlinear compliance curve that has a particular use in medical practice.

Another objective of the present invention is to provide a dual layer balloon, one having a high compliance curve and the other having a low compliance curve, that together combine to provide a nonlinear compliance curve.

SUMMARY OF THE INVENTION

To achieve these and other objectives, the present invention provides a new and unique balloon catheter that includes a two layered balloon that causes the balloon to have a nonlinear compliance curve.

Briefly, a preferred embodiment of the present invention includes a dual layered balloon, the outside balloon having a high compliance curve and a relatively small low pressure diameter, and the inside balloon having a low compliance curve and a relatively large low pressure diameter. Such a balloon catheter will have a non-linear compliance curve.

In another embodiment of the present invention the outside balloon is the Non-Compliant balloon and the inside balloon is the High-Compliant balloon. This embodiment can have the same nonlinear compliance curve as the previous embodiment but has the Non-Compliant balloon, made from relatively rigid or stiff polymeric materials, on the outside.

In a third embodiment of the present invention the outside balloon is a Compliant balloon having a low pressure diameter equal to or larger than the low pressure diameter of the inside Non-Compliant balloon.

An important advantage of the present invention is that a physician can select a balloon catheter that will perform certain desired functions when located in the vascular system and inflated to particular pressures. It is another advantage of the present invention that a physician will have a greater variety of balloon catheters to choose from that will have the capability to perform new functions or combinations of functions that formally required multiple balloon catheters.

These and other objects and advantages of the present invention will no doubt become apparent to those skilled in the art after having read the following detailed description of the preferred embodiment which are contained in and illustrated by the various drawing figures.

BRIEF DESCRIPTION OF DRAWING

In the Figures of the drawing, in which the double layered balloon is illustrated, there is a gap or space shown between the inner and outer balloon. This gap or space is for the purpose of clarity in illustrating the structure. The inner and outer balloons are bonded together at their distal and proximal ends after the space between them has been evacuated such that no air is sealed between them.

FIG. 5 is a cross-section view of the preferred embodiment prior to inflation.

FIG. 6 is a graph of the compliance curve of the FIG. 5 device, with the diameter of the balloon as the ordinate and the inflating pressure as the abscissa.

FIG. 7 is a cross-section view of a second embodiment, of the invention prior to inflation.

FIG. 8 is a cross-section view of the preferred embodiment inflated to a pressure slightly above the pressure required to inflate the outer High-Compliant balloon to its expanded diameter.

FIG. 9 is a graph of the compliance curve of the FIG. 8 device, with the diameter of the balloon as the ordinate and the inflating pressure as the abscissa.

FIG. 10 is a cross-section view of the second embodiment, inflated to a pressure slightly above the pressure required to inflate the inner High-Compliant balloon to its expanded diameter the expanded diameter of the High-Compliant inner balloon.

FIG. 11 is a cross-section view of the preferred embodiment inflated to the expanded pressure of the Non-Compliant balloon.

FIG. 12 is a graph of the compliance curve of the FIG. 11 device, with the diameter of the balloon as the ordinate and the inflating pressure as the abscissa.

FIG. 13 is a cross-section view of the second embodiment inflated to the expanded diameter of the Non-Compliant balloon.

DETAILED DESCRIPTION OF THE PREFERRED EMBODIMENT

The present invention will be illustrated and described as an over-the-wire balloon catheter for use in angioplasty. However it should be understood that the present invention can be applied to fixed-wire catheters including shortened guide wire lumens or to non-over-the-wire balloon catheters. Furthermore this invention can be used in balloon catheters intended for use in any and all vascular systems or cavities of the body.

Figure 3:
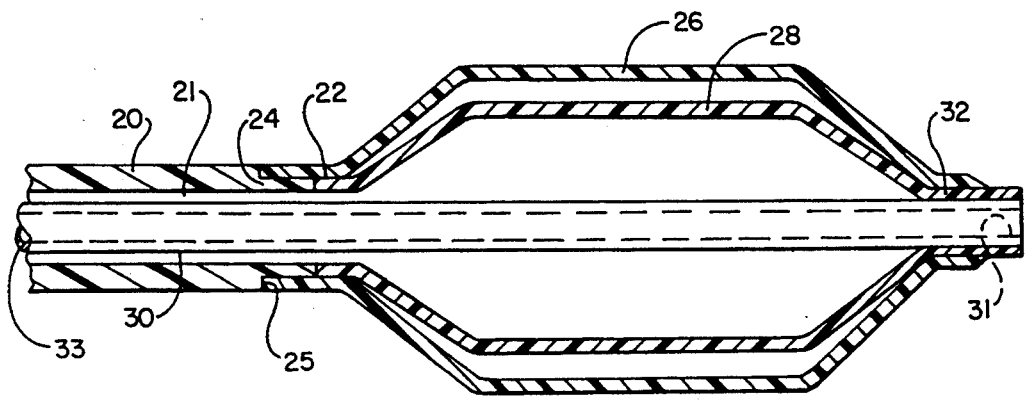
FIG. 3 shows a dilation catheter with the preferred embodiment of the invention, shown in cross-section.

Referring to FIG. 3 which shows the distal end of a balloon catheter having a dual layered balloon. The preferred embodiment of the invention will be described with reference to FIG. 3. Outer balloon 26 is constructed of material such as polyolefin or copolymers, for example Surlyn ®, PBT or polyethylene, such that this balloon has a high compliance curve. Outer balloon 26 has a smaller low pressure diameter than inner balloon 28. The inner balloon 28 is constructed of material such as poly(ethylene terephthalate) such that this balloon has a low compliance curve. Inner balloon 28 has a larger low pressure diameter than outer balloon 26. It should be understood that the diameters of the balloons 26 and 28 are not accurately reflected in the schematic view shown in FIG. 3.

The inner and outer balloons can be bonded together distally and proximally provided the space between them has been evacuated to insure that no air is sealed between them. If air is present between inner and outer balloons that have been bonded together at both ends then a gap will be created between the balloons which will remain during inflation and could cause unreliable sizing during use, and would increase the profile of the folded balloon.

Since outer balloon 26 has a smaller low pressure diameter than inner balloon 28 when the balloons are uninflated outer balloon 26 will have a smooth exterior when inflated.

The catheter is made up of an elongated outer plastic tube 20 having a distal end 24. The plastic tube 20 is preferably made of a flexible material such as a high density polyethylene. The elongated outer plastic tube 20 has a lumen 21 that functions as the inflation lumen and extends its entire length. There is a recessed area 25 at the distal end 24 into which the proximal end of the outer balloon 26 is secured. The outer balloon 26 and inner balloon 28 are each individually molded to a desired shape, size and wall thickness. The inner balloon 28 is folded down to minimize its diameter so that it can then be inserted into outer balloon 26. One end of the double layered balloon is bonded together, the air between the balloons is evacuated and then the other end of the double layered balloon is bonded together. The shape of outer balloon 26 and inner balloon 28 is generally cylindrical with reduced portions at each end. The proximal ends of outer balloon 26 and inner balloon 28 are coaxial and are bonded together at 22 and the two balloons are bonded to the recessed area 25 formed in the distal end 24 of the elongated outer plastic tube 20.

An elongated inner tube 30 is concentric with and within the elongated outer plastic tube 20. The inflation lumen 21 is defined by the inner surface of elongated outer plastic tube 20 and the outer surface of elongated tube 30. The distal end 31 of elongated inner tube 30 extends distally of the distal end 24 of elongated outer tube 20. The distal ends of outer balloon 26 and inner balloon 28 are coaxial and are adjacent to each other at 32 and to the distal end 31 of the elongated inner tube 30. The elongated inner tube 30 is hollow and thus forms a guide wire lumen 33. Since the low pressure diameter of an angioplasty balloon is generally greater than the diameter of the outer plastic tube 20 it is the usual practice to fold down the balloon and wrap it in the folded condition such that it will maintain a low-profile during uninflated use. Balloon catheters having a low profile are easier to manipulate through the patients vascular system and is particularly beneficial when passing the balloon through a tightly closed lesion.

Figure 1A:
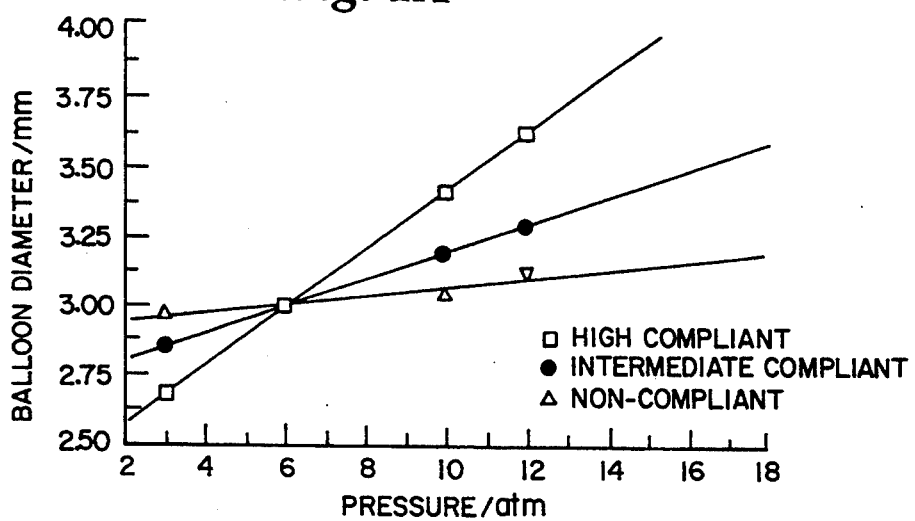
FIG. 1A is a graph showing compliance curves for several dilating catheters with the diameter of the balloon, measured in millimeters, as the ordinate and inflating pressure, measured in atmospheres, as the abscissa.
Figure 2B:
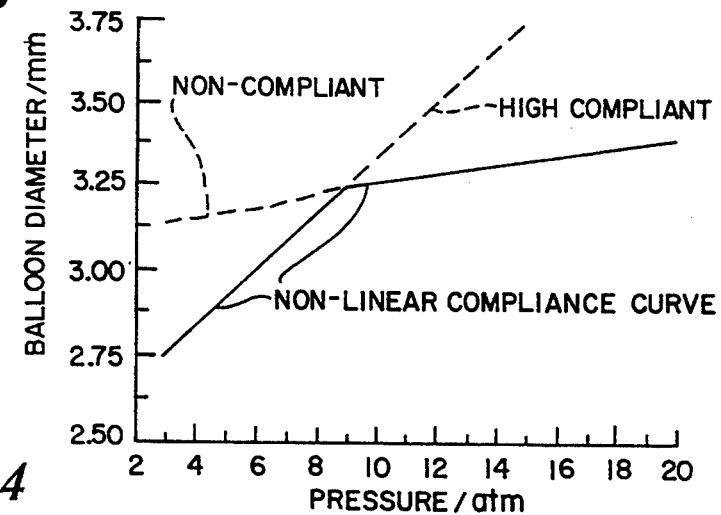
FIG. 2A is a graph, with balloon Diameter measured in millimeters as the ordinate and inflating pressure measured in atmospheres as the abscissa, on which is shown the compliance curve for two different balloons and also the combined nonlinear compliance curve.

Referring to FIG. 3, when inner balloon 28 is initially inflated, it causes outer balloon 26 to be inflated to its low pressure diameter. If increased pressure is applied to inner balloon 28 the diameter of outer balloon 26 will increase following its compliance curve. Outer balloon 26 being a High-Compliant balloon will have a compliance curve, as illustrated in FIGS. 1 and 2, conforming to a relatively steep straight line.

When inner balloon 28 has been inflated sufficiently that it has opened to its low pressure diameter the outer balloon 26 envelopes and complies to the inflated shape of inner balloon 28. Since inner balloon 28 has a larger low pressure diameter than outer balloon 26, inner balloon will be wrinkled during the initial stage of inflation. It should be understood that, at this point in the inflation process, outer balloon 26 is at its expanded diameter and would have expanded to this diameter in the absence of inner balloon 28. In the absence of inner balloon 28 a further pressure increase would cause balloon 26 to continue to increase in diameter following its relatively steep straight line compliance curve. However, further pressure increase will no longer result in outer balloon following its compliance curve, rather both balloons will follow the compliance curve of Non-Compliant inner balloon 28. As illustrated in FIGS. 1A and 2A low compliance curves are relatively shallow straight lines. Thus upon further increasing the pressure, both inner and outer balloons will follow the relatively shallow compliance curve of inner balloon 28. The result will be a small increase in the diameter of the combined balloon. Thus by increasing the pressure to inner balloon 28 the hardness and uniformity of the outer surface of the combined inflated balloon increases.

Figure 4:
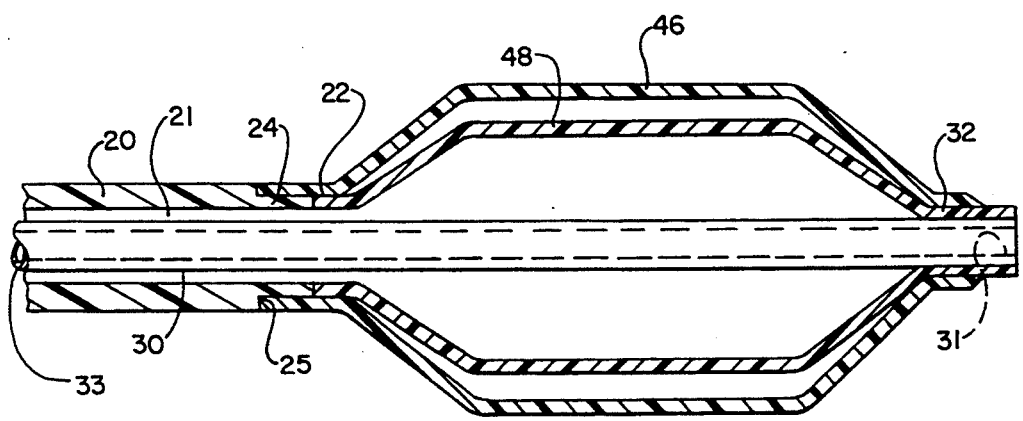
FIG. 4 shows a second embodiment of the invention, shown in cross-section.

Referring now to FIG. 4, which illustrates a second embodiment of the invention. In this embodiment the elongated outer plastic tube 20 and the elongated inner tube 30 are not changed and the same reference numerals are used for these elements that are the same. In this embodiment outer balloon 46 is a Non-Compliant balloon and inner balloon 48 is a High-Compliant balloon. The Non-Compliant balloon 46 has a larger low pressure diameter than the High-Compliant balloon 48.

Upon initial inflation of the inner High-Compliant balloon, it first opens up to its low pressure diameter which is smaller than the low pressure diameter of the outer Non-Compliant balloon 46. This initial inflation thus has no effect on the outer balloon 46. Upon increasing the pressure to the inner High-Compliant balloon it begins to increase in diameter following its high compliance curve. Inner balloon 48 continues to increase in diameter along its high compliance curve until it reaches a diameter that is equal to the low pressure diameter of the outer Non-Compliant balloon 46. At this point both balloons have substantially the same diameter. Upon applying additional pressure to inner balloon 48 both balloons will increase in diameter along the same curve. The curve that is followed is the non compliance curve of the outer balloon 46. Outer balloon 46 constrains the inner balloon from increasing along its high compliance curve. This embodiment, like the previous embodiment would be folded down and then wrapped to thus provide a low profile balloon prior to inflation.

Referring now to FIGS. 5 through 13 inclusive, which depict schematic views of the balloon catheter and corresponding pressure-diameter graphs, which will be used to discuss the inflation sequence of the preferred and a second embodiment.

In FIGS. 5, 7, 8, 10, 11 and 13 the cross sectional views of the balloons are illustrated as lines and the dimensions are not to scale. These schematic views are intended to emphasize the change in diameters of the balloons that occurs during an inflation cycle. Actually, when the balloons are not inflated they are collapsed and wrapped such that the profile of the balloon section of the catheter is approximately equal to the diameter of the outer elongated plastic tube 20. This small profile facilitates maneuvering the catheter through the vascular system.

FIGS. 5, 8 and 11 show a sequence in the inflation process of the preferred embodiment. FIG. 5 shows an inner Non-Compliant balloon 28 having a low pressure diameter of 2.5 millimeters. Surrounding inner balloon 28 is outer High-Compliant balloon 26 having a low pressure diameter of 2.0 millimeters. The proximal ends of balloons 26 and 28 are secured by bonding or the like to the distal end of outer elongated plastic tube 20. The distal ends of balloons 26 and 28 are secured by bonding or the like to the inner elongated tube 30. Although both of the balloons appear fully inflated in FIG. 5, this view is intended to represent the balloons after an initial low pressure of around two (2) atmospheres has been applied to the combination of both balloons. In reality, since the outer High-Compliant balloon 26 has a low pressure diameter of 2.0 millimeters, and the inner Non-Compliant balloon 28 has a low pressure diameter of 2.5 millimeters (if it were to be inflated independently without being constrained by the outer balloon), the inner Non-Compliant balloon 28 will exhibit some wrinkling and folding as it presses against the taut outer High-Compliant balloon 26.

FIG. 6 is a graph, corresponding to the condition of the balloons as seen in FIG. 5, showing balloon diameter in millimeters on the Y-axis and the inflation pressure in atmospheres on the X-axis.

FIG. 8, shows the diameter growth of the dual balloons of FIG. 5 as inflation pressure is increased to six (6) atmospheres, at which point the outer High-Compliant balloon 26 has grown from 2.0 millimeters to about 2.5 millimeters, and the inner Non-Compliant balloon 28 has just become taut, with its previously wrinkled surface now smooth. So at six atmospheres, both the inner and outer balloons have substantially the same diameter of about 2.5 millimeters. During that expansion, the dual balloon followed the compliance curve for the outer High-Compliant balloon 26. The growth of the dual balloon as it is inflated to six atmospheres is shown in FIG. 9.

FIG. 11, shows the dual balloons of FIG. 5 after additional pressure has been applied, in excess of six atmospheres. The pressure has been applied to twelve atmospheres, and has caused the diameter of the dual layered balloon to increase from 2.5 to about 2.58 millimeters, a modest increase of 0.08 millimeters as compared to the 0.5 increase from FIGS. 5 to FIG. 8. In FIG. 12, the compliance curve for this further increase is illustrated. The flatter growth of the dual balloon when pressurized from six to twelve atmospheres is due to the contribution from the Non-Compliant inner balloon 28, which is the balloon primarily responsible for containing the pressures above 6 atmospheres. The flatter portion of the curve in FIG. 12 is generally the same curve that the inner Non-Compliant balloon 28 would follow if it were inflated to the same pressures individually, without being surrounded by the outer High-Compliant balloon 26. The flatter portion of the curve in FIG. 12 is, however, slightly below the curve that the Non-Compliant balloon 28 would follow on its own, because the outer High-Compliant balloon 26 continues to exert an inward pressure on the inner Non-Compliant balloon 28 when the internal pressure of the dual balloon is above six atmospheres.

It should be noted that in this dual balloon example, 6 atmospheres, and 2.5 millimeters was the point at which the inflection in the curve of FIG. 12 occurred. However, it would be possible to design the sizes and compliance curves of each of the inner and outer balloons such that this inflection point could occur at different diameters and pressures.

Referring now to FIGS. 7, 10 and 13 which illustrates another embodiment of the invention. In the discussion of FIGS. 7, 10 and 13, FIGS. 6, 9 and 12 will also be referenced.

FIG. 7 differs from FIG. 5 in only one respect, in FIG. 7 the outer and inner balloons have been reversed. In FIG. 7 the Non-Compliant balloon 46 having a low pressure diameter of 2.5 millimeters is the outer balloon and the High-Compliant balloon 48 having a low pressure diameter of 2.0 millimeters is the inner balloon. As in FIG. 5 the balloons 46 and 48 are inflated sufficiently to open the inner High-Compliant balloon 48 to its low pressure diameter of 2.00 millimeters. So, in this embodiment, the outer Non-Compliant balloon 46 would be somewhat folded and wrinkled about the inner High-Compliant balloon 48 when a pressure of 2 atmospheres is applied to the inside of the dual balloon.

FIG. 10 illustrates the balloons, of FIG. 7, after six (6) atmospheres of pressure has been applied to stretch the inner High-Compliant balloon 48 from a low pressure diameter of 2.0 millimeters to its expanded diameter of 2.5 millimeters. In reaching this diameter, the wrinkles in the outer Non-Compliant balloon 46 would unfold until at six atmospheres the outer Non-Compliant balloon 46 would become just taut and would be of essentially the same diameter as the inner High-Compliant balloon 48, about 2.5 millimeters. It should be noted that the compliance curve shown in FIG. 9 applies equally to the dual balloon arrangement of both FIG. 8 and FIG. 10.

FIG. 13 depicts the dual layered balloon, of FIG. 7, after the pressure has been increased to twelve (12) atmospheres. In FIG. 13 the diameter of both the High-Compliant balloon 48 and Non-Compliant balloon 46 have been increased to 2.58 millimeters. The increased pressure above six atmospheres that was supplied to the dual balloon is taken up primarily by the Non-Compliant outer balloon 46. FIG. 12 shows the resultant compliance curve of the dual balloon of this embodiment when taken to pressures above six atmospheres. Again, as in the previous example, the flatter portion of the curve in FIG. 12 for this embodiment follows generally the same curve that the outer Non-Compliant balloon 46 would follow if it were individually pressurized. However, the flatter part of the curve in FIG. 12 is slightly below the curve the outer Non-Compliant balloon 46 would have on its own, because the inner High-Compliant balloon 48 helps to "absorb" some of the pressure contained within the dual balloon.

It should be noted that for this dual balloon example shown in FIG. 7, the location of the inflection in the curve of FIG. 12 for this embodiment could be different, depending on the sizing and compliance of the inner High-Compliant balloon 48 and the outer Non-Compliant balloon 46.

Figure 14:
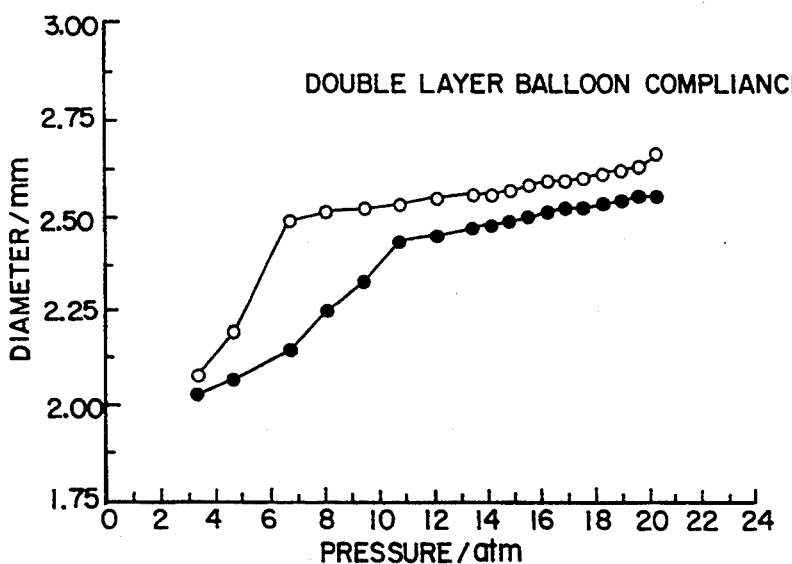
FIG. 14 is a graph of data from actual two layer balloons of the type shown in FIGS. 3-5, 7, 8, 10, 11 and 13.

FIG. 14 is a graph of data that was collected when two different two layer balloon of the type covered by this invention were inflated. In this Figure the balloon diameter, in millimeters, is plotted along the Y-axis and the pressure in atmospheres is plotted along the X-axis. The data points are shown by small circles, that are connected by lines to form the compliance curve for a particular balloon catheter. The data points for one two layered balloon are filled in and the data points for the other two layered balloon are not.

Figure 15:
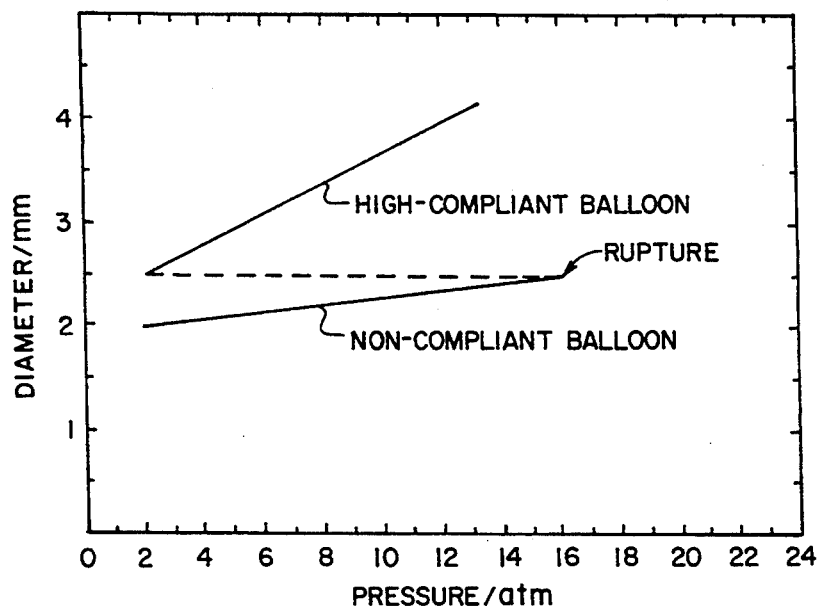
FIG. 15 is a graph showing compliance curves for compliant and non-compliant balloon used in a third embodiment.
Figure 16:
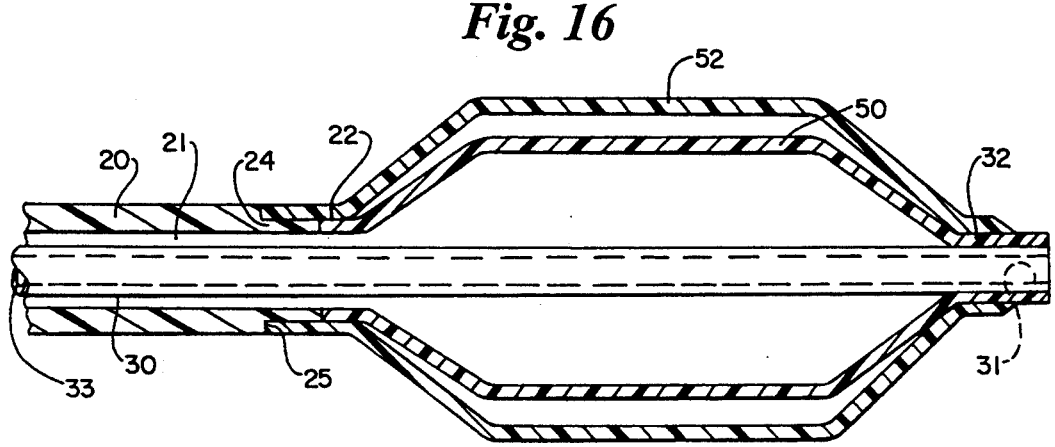
FIG. 16 shows a third embodiment of the dilation catheter, shown in cross-section.

Referring now to FIGS. 15 and 16 which disclose a third embodiment of the subject invention. The structure of this embodiment is similar to the structure of the preferred embodiment shown in FIG. 3 differing only in that in this embodiment the low pressure diameter of the inner Non-Compliant balloon 50 is about equal to or smaller than the low pressure diameter of the outer Compliant balloon 52. In this embodiment, at low inflation pressures neither balloon will be wrinkled. When in the initial inflation phase inflation fluid is metered through inflation lumen 21 to the inner Non-Compliant balloon 50, the relatively shallow slope section of the compliance curve labeled Non-Compliant in FIG. 15 is followed. Since the outer Compliant balloon 52 has a low pressure diameter equal to or greater than the low pressure diameter of inner balloon 50, the initial inflation phase has little or no effect on outer balloon 52. The Non-Compliant balloon 50 functions in the same manner as a conventional Non-Compliant balloon. If however the physician finds that the Non-Compliant balloon has not produced satisfactory results, i.e. the lesion recoils after deflation requiring an over dilatation to yield a satisfactory post recoil lumen diameter, and he or she now desires to use a Compliant balloon to dilate the restricted area, additional inflation fluid is metered to inner balloon until balloon 50 ruptures. It is important to understand that the inflation fluid used in angioplasty procedures is a non-compressible fluid. Accordingly when inner Non-Compliant balloon 50 ruptures, at for example at a pressure of 16 atmospheres as indicated in FIG. 15, there is a fixed volume of inflation fluid that is restricted within the lumen 21 and balloon 50. This volume of inflation fluid remains the same after the rupture of balloon 50. Upon the rupture of inner balloon 50 the inflation fluid will be contained by the outer Compliant balloon 52. However, because the low pressure diameter of outer Compliant balloon 52 is about equal to the low pressure diameter of inner Non-Compliant balloon 50 the pressure exerted by the fixed volume of inflation fluid on outer Compliant balloon 52 drops from 16 atmosphere toward zero atmosphere. As a result the compliance curve for this embodiment jumps from the point of rupture at the right hand end of the Non-Compliance curve (FIG. 15) to the left hand end of the compliance curve from the Compliant balloon. The secondary inflation phase is initiated with the metering of additional inflation fluid into the outer balloon 52 through inflation lumen 21. During this secondary inflation phase the relatively steep slop of the Compliant Curve is followed. In FIG. 15, the jump from the right hand end of the Non-Compliant Curve to the left hand end of the Compliant Curve is indicated by a dash line. An the inner balloon is to provide a separate inflation lumen to the outer balloon so that the outer balloon can be inflated independently of and without rupturing the inner balloon. Thus the complete compliance curve for this embodiment has an initial section that follows the shallow slope of the inner Non-Compliant balloon and then continues up the steeper slope of the outer Compliant balloon.

Although the present invention has been described in terms of specific embodiments, it is anticipated that alterations and modifications thereof will no doubt become apparent to those skilled in the art. It is therefore intended that the following claims be interpreted as covering all such alterations and modifications as fall within the true spirit and scope of the invention.

I claim:

1. A catheter useful for angioplasty comprising:
   an elongated catheter tube having a proximal and a distal end and a catheter tube circumference,
   a dilating element secured to the distal end of said elongated catheter tube and having an unexpanded circumference greater than the catheter tube circumference, said dilating element having a non-linear compliance curve, said compliance curve having a substantially linear compliant segment and a substantially linear segment of relatively less compliance, and said compliant segment having a slope corresponding to a diameter increase of no more than 10% per atmosphere of increased pressure,
   said elongated catheter tube having an inflation lumen extending from its proximal to its distal end, the distal end of said inflation lumen communicating with the interior of said dilating element,
   inflation means in communication with the proximal end of said inflation lumen for metering inflation fluid into the inflation lumen and the interior of said dilating element to cause the dilating element to expand in the diametric direction in accordance with its non-linear compliance curve.

2. The invention as set forth in claim 1 wherein the inflation means is operative to expand the dilating element during an initial inflation phase and a secondary inflation phase and the compliant segment of the compliance curve corresponds to the initial inflation phase of the catheter and the relatively less compliant segment corresponds to the secondary inflation phase of the catheter.

3. A catheter useful for angioplasty comprising:

an elongated catheter tube having a proximal and a distal end, a dilating element secured to the distal end of said elongated catheter tube, said dilating element having a non-linear compliance curve, said compliance curve having a substantially linear compliant segment and a substantially linear segment of relatively less compliance, and said compliant segment having a slope corresponding to a diameter increase of no more than 10% per atmosphere of increased pressure, said elongated catheter tube having an inflation lumen extending from its proximal to its distal end, the distal end of said inflation lumen communicating with the interior of said dilating element, inflation means in communication with the proximal end of said inflation lumen for metering inflation fluid into the inflation lumen and the interior of said dilating element to cause the dilating element to expand in the diametric direction in accordance with its non-linear compliance curve; and wherein the inflation means is operative to expand the dilating element during an initial inflation phase and a secondary inflation phase and the relatively less compliant segment corresponds to the initial inflation phase of the catheter and the relatively compliant segment corresponds to the secondary inflation phase of the catheter.

4. A catheter including a catheter tube and an inflatable balloon portion having a non-linear compliance curve within its usable range as a dilating element, the catheter comprising:

a first balloon, made of a compliant plastic material, having a first low pressure diameter, a second balloon, made of a low compliant plastic material, having a second low pressure diameter, said first and second balloons being coextensive and located one within the other and having an uninflated circumference greater than the circumference of the catheter tube, means, for inflating the inner of said balloons, in operative communication with the inner balloon, said first and second low pressure diameters being unequal such that the compliance curve of the first balloon will be followed during initial inflation until the diameter of the first balloon equals the low pressure diameter of the second balloon and the compliance curve of the second balloon will be followed during further inflation of the balloon portion of the catheter.

5. The invention as set forth in claim 4 wherein the first balloon, made of a compliant plastic material, is the outer balloon and the second balloon, made of a non-compliant plastic material, is the inner balloon.

6. The invention as set forth in claim 4 wherein the first balloon is made of a thermoplastic polymer.

7. The invention as set forth in claim 4 wherein the first balloon is made of a material selected from the group consisting of polyethylene, polyethylene blends, polyethylene copolymers, ionomers, polyesters, polyurethanes, polycarbonates, polyamides, polyvinyl chloride, acrylonitrile-butadiene-styrene copolymers, polyether-polyester copolymers, and polyether-polyamide copolymers.

8. The invention as set forth in claim 4 wherein the first balloon has a compliance curve which provides an increase in diameter of between 15% and 40% when expanded from said first low pressure diameter at 2 atmospheres pressure to an expanded diameter at 6 atmospheres pressure.

9. The invention as set forth in claim 4 wherein the first balloon has a compliance curve which provides an increase in diameter of between 15% and 40% when expanded from said first low pressure diameter at 2 atmospheres pressure to an expanded diameter at 12 atmospheres pressure.

10. The invention of claim 4 wherein the compliance curve of the balloon portion of the catheter has a segment which corresponds substantially to a segment of the compliance curve of the first balloon and which has a slope corresponding to an increase in diameter of no more than 10% per atmosphere of increased pressure.

11. The invention as set forth in claim 4 wherein the first balloon is made of a thermoplastic elastomer.

12. A catheter including an inflatable balloon portion having a non-linear compliance curve within its usable range as a dilating element, the catheter comprising:

a first balloon, made of a complaint plastic material, having a first low pressure diameter, a second balloon, made of a low compliant plastic material, having a second low pressure diameter, said first and second balloons being coextensive and located one within the other, means, for inflating the inner of said balloons in operative communication with the inner balloon, said first and second low pressure diameters being unequal such that the compliance curve of the first balloon will be followed during initial inflation until the diameter of the first balloon equals the low pressure diameter of the second balloon and the compliance curve of the second balloon will be followed during further inflation of the balloon portion of the catheter; and wherein the first balloon, made of a compliant plastic material, is the inner balloon and the second balloon, made of non-compliant plastic material, is the outer balloon.

13. A catheter including an inflatable balloon portion having a non-linear compliance curve, the catheter comprising:

a first balloon, made of compliant plastic material, having a first low pressure diameter, a second balloon, made of a non-compliant plastic material, having a second low pressure diameter, said balloon portion comprising said first and second balloons, said first and second balloons being located one within the other and said second balloon being the inner balloon, inflation means in operative communication with the inner balloon, the inflation means being operative to expand the balloon portion during an initial inflation phase and a secondary inflation phase, said first low pressure diameter being equal to or greater than the second low pressure diameter such that the compliance curve of the second balloon will be followed by the balloon portion during the initial inflation phase until the second balloon ruptures, and the compliance curve of the first balloon will be followed by the balloon portion during the secondary inflation phase of the balloon portion of the catheter.

14. A catheter including an inflatable balloon portion having a non-linear compliance curve, said balloon portion comprising first and second balloons, said first balloon having a first low pressure diameter and being formed of compliant plastic material, said second balloon having a second low pressure diameter and being formed of non-compliant plastic material, the low pressure diameter of the first balloon being equal to or greater than the low pressure diameter of the second balloon, said first and second balloons being located one within the other such that the first balloon is the outer balloon and the second balloon is the inner balloon, inflation means in operative communication with the second balloon, the inflation means being operative to expand the balloon portion during an initial inflation phase and a secondary inflation phase by metering an inflation fluid into the second balloon, the low pressure diameters of the first and second balloons and their relative locations one within the other being, such that during the initial inflation phase during which inflation fluid is metered to the interior of the second balloon, the second balloon will be inflated and the compliance curve of the second balloon will be followed by the balloon portion until the second balloon ruptures, thereby bringing the inflation means into communication with the first balloon, and whereupon the pressure in the balloon portion is reduced and further metering inflation fluid to the interior of the first balloon will cause the balloon portion to follow the compliance curve of the first balloon.

15. A catheter including a catheter tube and an inflatable balloon portion having a non-linear compliance curve within its usable range as a dilating element, the catheter comprising:

a first balloon, made of a compliant plastic material, having a first low pressure diameter and proximal and distal ends, a second balloon, made of a low compliant plastic material, having a second low pressure diameter and proximal and distal ends, said first and second balloons being coextensive and located one within the other and connected at the proximal and distal ends, the balloons having an uninflated circumference greater than the circumference of the catheter tube, means, for inflating the inner of said balloons, in operative communication with the inner balloon, said first and second low pressure diameters being unequal such that the compliance curve of the first balloon will be followed during initial inflation until the diameter of the first balloon equals the low pressure diameter of the second balloon and the compliance curve of the second balloon will be followed during further inflation of the balloon portion of the catheter.

16. A method of using an angioplasty balloon catheter, the catheter comprising a catheter tube and a balloon portion having a non-linear compliance curve within its useful range as an angioplasty balloon, the balloon portion of the catheter having inner and outer balloons having unequal low pressure diameters enveloped one within the other and having a greater uninflated circumference than the circumference of the catheter tube, one of said balloons being made of compliant material and the other being made of non-compliant material, comprising the steps of:

(a) pressurizing the inner balloon to a first inflation pressure to inflate the balloon made of compliant material beyond its low pressure diameter such that the balloon section of the catheter increases in diameter, in response to this step, to a first predetermined diameter along the compliance curve of the compliant material which corresponds to said first inflation pressure, and then (b) increasing the pressure supplied to the inner balloon to a second inflation pressure sufficient to inflate the balloon made of non-compliant material beyond its low pressure diameter such that the balloon section of the catheter increases in diameter, in response to this step, to a second predetermined diameter along the compliance curve of the non-compliant material which corresponds to said second inflation pressure.

17. A method of using a balloon catheter having a non-linear compliance curve as set forth in claim 16, wherein the outer balloon is the compliant balloon and the inner balloon is the non-compliant balloon.

18. The method as set forth in claim 16 wherein the balloon made of a compliant plastic material is made of a thermoplastic polymer.

19. The method as set forth in claim 16 wherein the balloon made of a compliant plastic material is made of a material selected from the group consisting of polyethylene, polyethylene blends, polyethylene copolymers, ionomers, polyesters, polyurethanes, polycarbonates, polyamides, polyvinyl chloride, acrylonitrile-butadiene-styrene copolymers, polyether-polyester copolymers, and polyether-polyamide copolymers.

20. The method as set forth in claim 16 wherein the balloon made of a compliant material has a compliance curve which has a slope corresponding to an increase in diameter of between 15% and 40% when expanded from said first low pressure diameter at 2 atmospheres pressure to an expanded diameter at 6 atmospheres pressure.

21. The method as set forth in claim 16 wherein the balloon made of a compliant material has a compliance curve which has a slope corresponding to an increase in diameter of between 15% and 40% when expanded from said first low pressure diameter at 2 atmospheres pressure to an expanded diameter at 12 atmospheres pressure.

22. The method of claim 16 wherein the compliance curve of the balloon portion of the catheter has a segment which corresponds substantially to a segment of the compliance curve of the balloon made of a compliant material and which has a slope corresponding to an increase in diameter of no more than 10% per atmosphere of increased pressure.

23. The invention as set forth in claim 16 wherein the balloon made of a complaint plastic material is made of a thermoplastic elastomer.

24. A method of using an angioplasty balloon catheter, the catheter comprising a balloon portion having a non-linear compliance curve within its useful range as an angioplasty balloon, the balloon portion of the catheter having inner and outer balloons having unequal low pressure diameters enveloped one within the other, one of said balloons being made of compliant material and the other being made of non-compliant material, comprising the steps of:

(a) pressurizing the inner balloon to a first inflation pressure to inflate the balloon made of compliant material beyond its low pressure diameter such that the balloon section of the catheter increases in diameter in response to this step, to a first predetermined diameter along the compliance curve of the compliant material which corresponds to said first inflation pressure, and then (b) increasing the pressure supplied to the inner balloon to a second inflation pressure sufficient to inflate the balloon made of non-compliant material beyond its low pressure diameter such that the balloon section of the catheter increases in diameter, in response to this step, to a second predetermined diameter along the compliance curve of the non-compliant material which corresponds to said second inflation pressure; and (c) wherein the balloon made of a compliant plastic material, is the inner balloon and the balloon made of non-compliant plastic material, is the outer balloon.

25. A method of dilating a restricted zone in a blood vessel using a balloon catheter including a catheter tube comprising the steps of:

(a) locating an uninflated balloon portion of the balloon catheter in a blood vessel such that the uninflated balloon portion crosses the restricted zone, the balloon portion having an uninflated circumference greater than the circumference of the catheter tube and a non-linear compliance curve including high compliance and low compliance portions within the useable range of the balloon portion as a dilation element for said vessel;

(b) metering inflation fluid to the interior of the balloon portion, causing the diameter of the balloon to increase to a desired diameter along the high compliance portion of the curve;

(c) increasing the pressure being applied to the inflation fluid being metered to the interior of the balloon portion such that further increase in the balloon diameter above the desired diameter will follow the low compliance portion of the curve.

26. A method of dilating a restricted zone in a blood vessel with a balloon catheter having a balloon inflation portion including a non-compliant inner balloon within a compliant outer balloon comprising the steps of:

(a) locating the balloon inflation portion of the balloon catheter in a blood vessel such that the balloon inflation portion crosses the restricted zone;

(b) metering inflation fluid to the interior of the inner balloon at controlled pressures, causing the diameter of the balloon inflation portion to increase to a desired diameter along the compliance curve of the inner balloon;

(c) increasing the metering of inflation fluid to the interior of the inner balloon such that the inner balloon is ruptured and the inflation fluid is brought into communication with the outer balloon, (d) further metering inflation fluid to the outer balloon such that the diameter of the balloon inflation portion increases following the compliance curve of the outer compliant balloon.

27. A method of dilating one or more restricted zones in a blood vessel using a catheter having a catheter tube and a balloon dilating element located at the distal end of the catheter, the dilating element having a non-linear compliance curve, the compliance curve having first and second segments of different slope providing available inflated diameters for said dilating element, one of said segments being a compliant segment and the other being a non-compliant segment, the method comprising:

(a) locating the uninflated balloon dilating element across a restricted zone in a blood vessel, the uninflated balloon dilating element having greater circumference than the catheter tube circumference;

(b) selecting a first inflated diameter from the diameters available along said first segment and a first pressure corresponding to said first diameter on said non-linear compliance curve;

(c) pressurizing the dilating element to the selected first pressure so as to dilate the restricted zone then crossed by the dilating element;

(d) selecting a second inflated diameter from the diameters available along the second of said segments and a second pressure corresponding to said diameter on said non-linear compliance curve; and (e) pressurizing the dilating element to the second pressure while the balloon is located across the same or a different restricted zone so as to dilate the restricted zone then crossed by the dilating element.

28. The method of claim 27 wherein said pressurizing steps (c) and (e) are conducted while the dilating element is located across the same restricted zone.

29. The method of claim 27 wherein said first segment is a compliant curve segment and said second segment is a non-compliant curve segment.

30. The method of claim 27 wherein the diameters available on said first segment are higher than the diameters available on said second segment.

31. A method of dilating one or more restricted zones in a blood vessel using a catheter having a balloon dilating element located at the distal end of the catheter, the dilating element having a non-linear compliance curve, the compliance curve having first and second segments of different slope providing available inflated diameters for said dilating element, one of said segments being a compliant segment and the other being a non-compliant segment, the method comprising:

(a) locating the uninflated balloon dilating element across a restricted zone in a blood vessel;

(b) selecting a first inflated diameter from the diameters available along said first segment and a first pressure corresponding to said first diameter on said non-linear compliance curve;

(c) pressurizing the dilating element to the selected first pressure so as to dilate the restricted zone then crossed by the dilating element;

(d) selecting a second inflated diameter from the diameters available along the second of said segments and a second pressure corresponding to said diameter on said non-linear compliance curve; and (e) pressurizing the dilating element to the second pressure while the balloon is located across the same or a different restricted zone so as to dilate the restricted zone then crossed by the dilating element; and (f) wherein between said pressurizing steps (c) and (e), the balloon is relocated across a different restricted zone.

32. A method of dilating one or more restricted zones in a blood vessel using a catheter having a balloon dilating element located at the distal end of the catheter, the dilating element having a non-linear compliance curve, the compliance curve having first and second segments of different slope providing available inflated diameters for said dilating element, one of said segments being a compliant segment and the other being a non-compliant segment, the method comprising;
(a) locating the uninflated balloon dilating element across a restricted zone in a blood vessel;
(b) selecting a first inflated diameter from the diameters available along said first segment and a first pressure corresponding to said first diameter on said non-linear compliance curve;
(c) pressurizing the dilating element to the selected first pressure so as to dilate the restricted zone then crossed by the dilating element;
(d) selecting a second inflated diameter from the diameters available along the second of said segments and a second pressure corresponding to said diameter on said non-linear compliance curve; and
(e) pressurizing the dilating element to the second pressure while the balloon is located across the same or a different restricted zone so as to dilate the restricted zone then crossed by the dilating element; and
(f) said first segment is a non-compliant curve segment and said second segment is a compliant curve segment.

* * * * *